United States Patent [19]

Merlen et al.

[11] Patent Number: 6,057,486
[45] Date of Patent: May 2, 2000

[54] CATALYST CONTAINING A ZEOLITE EUO AND THE USE OF THE CATALYST IN A PROCESS FOR ISOMERIZING AROMATIC COMPOUNDS CONTAINING 8 CARBON ATOMS PER MOLECULE

[75] Inventors: Elisabeth Merlen, Rueil Malmaison; Fabio Alario, Neuilly sur Seine; Sylvie Lacombe, Rueil Malmaison; Eric Benazzi, Chatou; Jean-François Joly, Lyons, all of France

[73] Assignee: Institut Francais du Petrole, Rueil-Malmaison Cedex, France

[21] Appl. No.: 09/218,181

[22] Filed: Dec. 22, 1998

Related U.S. Application Data

[60] Provisional application No. 60/075,109, Feb. 18, 1998, and provisional application No. 60/075,110, Feb. 18, 1998.

[30] Foreign Application Priority Data

Dec. 22, 1997 [FR] France ................................... 97 16458
Dec. 22, 1997 [FR] France ................................... 97 16456

[51] Int. Cl.⁷ ...................................................... C07C 5/22
[52] U.S. Cl. ........................... 585/481; 585/482; 502/64; 502/66; 502/74
[58] Field of Search ................................. 585/481, 482; 502/60, 64, 66, 74

[56] References Cited

U.S. PATENT DOCUMENTS 4,593,138  6/1986  Casci et al. ............................. 585/481
4,741,891  5/1988  Casci et al. ............................. 423/277

FOREIGN PATENT DOCUMENTS 0 051 318  5/1982  European Pat. Off. .
0 055 045  6/1982  European Pat. Off. .
0 537 389  4/1993  European Pat. Off. .
96/16004   5/1996  WIPO .

*Primary Examiner*—Tom Dunn
*Attorney, Agent, or Firm*—Millen, White, Zelano & Branigan, P.C.

[57] ABSTRACT

The invention concerns a catalyst comprising at least one zeolite with structure type EUO for example EU-1, at least partialy in its acid form, at least one matrix, and at least one metal from group VIII of the periodic table. the zeolite comprising silicon and at least one element T selected from the group formed by aluminium, iron, gallium and boron (preferably aluminium and boron), with a global Si/T atomic ratio over 5, the catalyst being characterized in that the dispersion of the group VIII metal is in the range 50% to 100%, limits included, and the macroscopic distribution coefficient of the group VIII metal is in the range 0.7 to 1.3, limits included, the catalyst having a mechanical strength such that the bed crush strength is more than 0.7 MPa. The invention also relates to the preparation of the catalyst and to the use of the catalyst in a process for isomerizing aromatic compounds containing 8 carbon atoms per molecule.

37 Claims, No Drawings

CATALYST CONTAINING A ZEOLITE EUO AND THE USE OF THE CATALYST IN A PROCESS FOR ISOMERIZING AROMATIC COMPOUNDS CONTAINING 8 CARBON ATOMS PER MOLECULE

CROSS-REFERENCE TO RELATED APPLICATIONS

This application is a regular application related under 35 U.S.C. 119(e) to provisional applications Ser. Nos. 60/075,109 and 60/075,110, both filed on Feb. 18, 1998.

FIELD OF THE INVENTION

The invention relates to a catalyst comprising at least one zeolite with structure type EUO, for example EU-1 zeolite, at least partially in its acid form, at least one matrix (binder), at least one element from group VIII of the periodic table ("Handbook of Physics and Chemistry", $76^{th}$ edition), optionally at least one metal from the group formed by groups IIIA and IVA of the periodic table, and optionally sulphur, the zeolite comprising silicon and at least one element T selected from the group formed by aluminium, iron, gallium and boron, preferably aluminium and boron, with a global Si/T atomic ratio over 5, preferably in the range 5 to 100, limits included, the group VIII metal preferably being deposited on the matrix with good dispersion on the catalyst surface and macroscopically with good distribution through the grain of the catalyst. Further, this formed catalyst, for example in the form of balls or extrudates, has good mechanical strength.

BACKGROUND OF THE INVENTION

The invention also relates to the use of the catalyst in a process for isomerizing aromatic compound containing 8 carbon atoms per molecule.

Isomerisation of ethylbenzene to xylenes requires the presence of a group VIII metal. Optimised formulations based on mordenite and a group VIII metal have produced catalysts wherein side reactions remain non negligible. Examples are naphtene ring opening followed or otherwise by cracking, or dismutation and transalkylation of $C_8$ aromatics which lead to the formation of unwanted aromatics. The development of more selective novel catalysts is thus of particular importance.

ZSM-5 is one zeolite which is used for isomerisation of $C_8$ aromatic cuts, used alone or mixed with other zeolites such as mordenite. Such catalysts have been described in United States patents U.S. Pat. No. 4,467,129, U.S. Pat. No. 4,482,773 and European patent EP-B-0 138 617. Other catalysts are based on mordenite and have been described in U.S. Pat. No. 4,723,051, U.S. Pat. No. 4,665,258 and French patent FR-A-2 477 903.

The lack of selectivity of mordenite can be attenuated by optimising specific treatments and/or formulations as described, for example, in our French patent FR-A-2 691 914. Such techniques can reduce dismutation side reactions.

EU-1 zeolite with structure type EUO, which has already been described in the prior art, has a unidimensional microporous framework, with a pore diameter of 4.1×5.7 Å (1 Å=1 Angström=$10^{-10}$ m) ("Atlas of Zeolite Structure Types", W. M. Meier and D. H. Olson, $4^{th}$ edition, 1996). Further, N. A. Briscoe et al. stated in their article in the review Zeolites (1988, 8, 74) that such unidimensional channels have lateral pockets with a depth of 8.1 Å and a diameter of 6.8×5.8 Å. A method for synthesising EU-1 zeolite and its physico-chemical characteristics have been described in European patent EP-B 1-0 042 226. United States patent U.S. Pat. No. 4,640,829 relates to ZSM-50 zeolite which, according to the "Atlas of Zeolite Structure Types", W. M. Meier and D. H. Olson, $4^{th}$ edition, 1996, has the same EUO structure type as EU-1 zeolite. That patent describes a method for synthesising ZSM-50 which is different from that described in EP-B1-0 042 226 for EU-1 zeolite. EP-A1 0 051 318 relates to TPZ-3 zeolite which, according to the "Atlas of Zeolite Structure Types", W. M. Meier and D. H. Olson, $4^{th}$ edition, 1996, has the same EUO structure type as EU-1 zeolite, and its use as a catalyst containing zeolite as it is or formed. In that document, forming of the TPZ-3 zeolite is exemplified by preparing pellets, obtained by pelletizing a mechanical mixture of zeolite powders and a binder. The pellets contain the TPZ-3 zeolite, a binder and optionally at least one element selected from the group formed by iron, cobalt, nickel, copper, zinc, ruthenium, rhodium, palladium, rhenium, osmium, iridium and platinum, as the metal or metal oxide.

SUMMARY OF THE INVENTION

We have surprisingly discovered a formed catalyst comprising:
  at least one zeolite with structure type EUO, for example EU-1 zeolite, at least partly and preferably practically completely in its acid form, containing silicon and at least one element T selected from the group formed by aluminium, iron, gallium and boron, preferably aluminium and boron, and such that the global Si/T atomic ratio is over 5, preferably in the range about 5 to 100, limits included;
  at least one matrix (binder), for example alumina;
  at least one element from group VIII of the periodic table;
  optionally, at least one metal from the group formed by groups IIIA and IVA of the periodic table;
  and optionally sulphur;
  said catalyst being characterized in that:
    the dispersion of the group VIII metal or metals, determined by chemisorption, for example $H_2$-$O_2$ titration or carbon monoxide chemisorption, is in the range 50% to 100%, limits included, preferably 60% to 100%, limits included, more preferably 70% to 100%, limits included;
    the macroscopic distribution coefficient of said metal (s), obtained from its profile determined using a Castaing microprobe, defined as the ratio of the concentrations of said metal in the grain core to that at the edge of the same grain, is in the range 0.7 to 1.3, limits included, preferably 0.8 to 1.2, limits included.
    the bed crush strength, determined using the Shell method (SMS 1471–74) is of more than 0.7 MPa.

The catalyst has excellent catalytic performances for the transformation of hydrocarbons such as isomerisation of an aromatic $C_8$ cut, i.e., mixtures constituted by xylenes and possibly ethylbenzene.

More particularly, the matrix (binder) consists of at least one element selected from the group formed by natural clays (such as kaolin or bentonite), synthetic clays, magnesia, aluminas, silicas, silica-aluminas, titanium oxide, boron oxide, zirconia, aluminium phosphates, titanium phosphates, and zirconium phosphates, preferably from elements of the group formed by aluminas and clays.

The zeolite with structure type EUO, preferably EU-1 zeolite, comprised in the catalyst of the invention is at least partially, preferably practically completely, in its acid form, i.e., in its hydrogen (H⁺) form, the sodium content preferably being such that the Na/T atomic ratio is below 0.5, preferably below 0.1, and more preferably below 0.02.

More particularly, the catalyst of the invention contains:

1% to 90% by weight, limits included, preferably 3% to 60%, limits included, to more preferably 4% to 40%, limits included, of at least one zeolite with structure type EUO, for example EU-1 zeolite, at least partially in its acid form, containing silicon and at least one element T selected from the group formed by aluminium, iron, gallium and boron, preferably aluminium and boron, wherein the global Si/T atomic ratio is over 5, preferably is in the range 5 to 100, limits included, more preferably 5 to 80, limits included, at least one element from group VIII of the periodic table, preferably selected from the group formed by platinum and palladium, more preferably platinum. The weight content of the element(s) is generally in the range 0.01% to 2.0%, limits included, preferably in the range 0.05% to 1.0%, limits included. The dispersion of the group VIII element(s), determined by chemisorption, is in the range 50% to 100%, limits included, preferably in the range 60% to 100%, limits included, more preferably in the range 70% to 100%, limits included. The macroscopic distribution coefficient of the group VIII element(s), calculated from its profile determined using a Castaing microprobe, said coefficient being defined as the ratio of the concentration of said group VIII element(s) in the grain core with respect to that at the edge of the same grain, is in the range 0.7 to 1.3, limits included, preferably in the range 0.8 to 1.2, limits included;

optionally, at least one additional element selected from the group formed by groups IIIA and IVA of the periodic table, preferably selected from the group formed by indium and tin. The weight content of the element(s) is generally in the range 0.01% to 2.0%, limits included, preferably in the range 0.05% to 1.0%, limits included;

optionally sulphur, the content of which is such that the ratio of the number of sulphur atoms to the number of atoms of deposited group VIII metal is in the range 0.5 to 2, limits included;

at least one matrix, or binder, forming the complement of the catalyst to 100%.

The catalyst has a bed crush strength of more than 0.7 MPa, determined using the Shell method (SMS 1471–74) which characterises it mechanical strength.

Deposition of at least one group VIII element is carried out so that the dispersion of the element(s), determined by chemisorption, is in the range 50% to 100%, limits included, preferably in the range 60% to 100%, limits included, and more preferably in the range 70% to 100%, Limits included. When at least one element from group VIII of the periodic table and optionally at least one element from groups IIIA and IVA are introduced after the zeolite with structure type EUO, for example EU-1 zeolite, has been formed, for example into balls or extrudates, it is important to obtain good distribution of the elements in the formed catalyst. This distribution is characterized by its profile obtained using a Castaing microprobe. The ratio of the concentrations of each group VIII element in the grain core with respect to that at the edge of the same grain, defined as the distribution coefficient, must be in the range 0.7 to 1.3, limits included, preferably in the range 0.8 to 1.2, limits included.

The invention also relates to the preparation of the catalyst. The catalyst of the invention is prepared by first treating a zeolite with structure type EUO, for example as synthesised EU-1 zeolite, using any method which is known to the skilled person, for example calcining in a stream of dry air to eliminate the organic template occluded in the zeolite microporosity, then carrying out at least one ion exchange step using, for example, at least one NH₄NO₃ solution, to eliminate at least some, preferably practically all alkaline cations, in particular sodium, present in the cationic position in the zeolite.

The catalyst preparation is continued by mixing the matrix and zeolite prepared as above, then forming. The catalyst of the invention is preferably formed into extrudates or balls, depending on its use. The zeolite forming conditions, choice of matrix, optional prior grinding of the zeolite, peptising, addition of poreforming agents, mixing time, extrusion pressure if the catalyst is formed into extrudates, the drying rate and duration, are determined for each matrix in accordance with rules which are well known to the skilled person, to obtain a catalyst which is preferably in the form of extrudates or balls.

The catalyst preparation is generally continued by calcining, normally at a temperature which is in the range 250° C. to 600° C. limits included, preferably preceded by drying, for example oven drying, at a temperature which is generally in the range from ambient temperature to 250° C., limits included, preferably in the range 40° C. to 200° C., limits included. The drying step is preferably carried out during the temperature rise required to carry out the calcining.

The zeolite with structure type EUO of the invention, for example EU-1 zeolite, can be formed from as synthesised zeolite, i.e., containing the organic template and alkaline cations, generally sodium. In this case calcining in dry air to eliminate the organic template, and the ion exchange steps using at least one NH₄NO₃ solution, are carried out on the formed catalyst comprising the zeolite and matrix.

The catalyst obtained after calcining and in the form of balls or extrudates has mechanical properties such that the bed crush strength, determined using the Shell method (SMS 1471–74), is over 0.7 MPa.

Deposition of at least one element from group VIII of the periodic table, and optionally at least one element selected from the group formed by groups IIIA and IVA of the periodic table, can be carried out at any time during the preparation, either before forming, or when mixing the zeolite and matrix, the zeolite being mixed with the ensemble constituted by the precursor(s) of the element(s) and the matrix or, as is preferred, after forming.

When at least one element selected from group VIII and optionally at least one element selected from the group formed by groups IIIA and IVA are added after forming, the element(s) can then be added either before calcining or, as is preferable, after calcining the matrix-zeolite mixture. The added element(s) are generally deposited either practically completely on the zeolite or partly on the zeolite and partly on the matrix, or, as is preferable, practically completely on the matrix, this being carried out in known manner by appropriate choice of the parameters used during deposition, such as the nature of the precursor of the element(s). Deposition of at least one group VIII element is generally carried out using dry impregnation, excess impregnation, or as is preferable by ion exchange(s). In the case of ion exchange from precursors based on platinum and/or palladium, platinum and/or palladium salts are generally used such as hexachloroplatinic acid an/or hexachloropalladic acid in the presence or absence of competing agents such as hydrochloric acid. In the case where at least one other metal selected from the group formed by groups IIIA and IVA of the periodic table is also introduced, any of the depositing techniques known to the skilled person and any of the precursors are suitable for introducing the additional metal.

When the catalyst contains a plurality of elements from group VIII of the periodic table, the metals can be introduced either all in the same manner or by using different techniques, and in any order. When at least one metal selected from the group formed by groups IIIA and IVA of the periodic table is also introduced, the elements from group VIII and groups IIIA and IVA can be introduced either separately or simultaneously in at least one single step. When at least one group IIIA or IVA element is added separately, it is preferably added prior to the group VIII element(s). When the depositing technique used is ion exchange, a plurality of successive ion exchange steps may be necessary to introduce the required quantities of metals.

Platinum is generally introduced into the matrix in the form of hexachloroplatinic acid, but ammoniacal compounds or compounds such as ammonium chloroplatinate, dicarbonyl platinum dichloride, hexahydroxyplatinic acid, palladium chloride, or palladium nitrate can also be used to introduce any noble metal.

In the present invention, the use of at least one noble metal from the platinum family can, for example, be via the use of ammoniacal compounds. In this case, the noble metal is deposited on the zeolite.

Examples for platinum are platinum II tetramine salts with formula $Pt(NH_3)_4X_2$, platinum IV hexamine salts with formula $Pt(NH_3)_6X_4$; platinum IV halogenopentamine salts with formula $(PtX(NH_3)_5)X_3$; platinum N tetrahalogenodiamine salts with formula $PtX_4(NH_3)_2$; platinum complexes with halogen-polyketones and halogenated compounds with formula $H(Pt(acac)_2X$; where X is a halogen selected from the group formed by chlorine, fluorine, bromine and iodine, X preferably being chlorine, and acac represents the group $C_5H_7O_2$ derived from acetylacetone.

The noble metal from the platinum family is preferably introduced by impregnation using an aqueous or organic solution of one of the organometallic compounds cited above. Suitable organic solvents are paraffinic, naphthenic or aromatic hydrocarbons, and halogenated organic compounds containing, for example, 1 to 12 carbon atoms per molecule. Examples are n-heptane, methylcyclohexane, toluene and chloroform. Mixtures of solvents can also be used.

The additional metal which is optionally also introduced, selected from the group formed by group IIIA and IVA elements, can be introduced by means of compounds such as chlorides, bromides and nitrates, alkyls of group IIIA and IV elements, namely tin and indium, for example, tin alkyls, and indium chloride and nitrate.

If this metal is introduced before the noble metal, the metal compound used is generally selected from the group formed by the metal halide, nitrate, acetate, tartrate, carbonate and oxalate. This introduction is thus advantageously carried out in an aqueous solution. However, it can also be introduced using a solution of an organometallic compound of the metal, for example terabutyltin. In this case, before proceeding to introducing at least one noble metal, calcining in air is carried out.

This metal can also be introduced in the form of at least one organic compound selected from the group formed by complexes of the metal, in particular polyketone complexes of the metal and hydrocarbyl metals such as metal alkyls, cycloalkyls, aryls, alkylaryls and arylalkyls. In the latter case, the metal is advantageously introduced using a solution of an organometallic compound of the metal in an organic solvent. Organohalogenated compounds of the metal can also be used. Particular examples of metal compounds are tetrabutyltin for tin, and triphenylindium for indium.

The impregnating solvent is selected from the group formed by paraffinic, naphthenic or aromatic hydrocarbons containing 6 to 12 carbon atoms per molecule and halogenated organic compounds containing 1 to 12 carbon atoms per molecule. Examples are n-heptane, methylcyclohexane and chloroform. Mixtures of the solvents defined above can also be used.

Deposition of at least one group VIII element and optionally at least one group IIIA or IVA element is preferably followed by calcining in air or oxygen, generally between 250° C. and 600° C., limits included, preferably between 350° C. and 550° C., limits included, for a period which is in the range 0.5 to 10 hours, limits included, preferably in the range 1 to 4 hours, limits included. This can optionally be followed by reduction in hydrogen, generally at a temperature in the range 300° C. to 600° C., preferably in the range 350° C. to 550° C., limits included, and for a period which is in the range 1 to 10 hours, limits included, preferably in the range 2 to 5 hours, limits included, to obtain the elements principally in the reduced form required for catalytic activity.

As an example, one preferred method for preparing the catalyst of the invention consists of mixing at least one zeolite with structure type EUO, for example EU-1 zeolite, in a moist matrix gel (generally obtained by mixing at least one acid and a powdered matrix), for example alumina, for the period required to obtain good homogeneity in the paste, namely for about ten minutes, then passing the paste through a die to form extrudates, for example with a diameter which is in the range 0.4 to 4 mm, limits included, preferably in the range 0.4 to 2.5 mm, limits included, and more preferably in the range 0.8 to 2.0 mm, limits included. Then, after drying for several hours at about 120° C. in an oven and after calcining, for example for about 2 hours at about 400° C., the group VIII element(s) and optionally the group IIIA and IVA elements, for example platinum, are deposited, for example by ion exchange, using hexachloroplatinic acid in the presence of a competing agent (for example hydrochloric acid), deposition being followed by calcining, for example for about 2 hours at about 400° C.

When the catalyst of the present invention contains sulphur, the sulphur is introduced into the formed and calcined catalyst containing the element(s) cited above, either in situ before the catalytic reaction, or ex situ. Sulphurisation is carried out using any sulphurising agent which is known to the skilled person, such as dimethyl disulphide or hydrogen sulphide. Optional sulphurisation occurs after reduction. With in situ sulphurisation, reduction (if the catalyst has not already been reduced) occurs before sulphurisation. For ex situ sulphurisation, reduction is carried out then sulphurisation.

In addition to excellent mechanical crush strength, the catalyst of the present invention has excellent catalytic performances for hydrocarbon transformations, such as isomerisation of aromatic compounds containing 8 carbon atoms, i.e., mixtures constituted by xylenes and possibly ethylbenzene. In fact the invention also relates to a process for isomerizing aromatics compounds containing 8 carbon atoms per molecule. The operating conditions of the process are generally as follows:

a temperature in the range 300° C. to 500° C., limits included, preferably in the range 320° C. to 450° C., limits included, more preferably in the range 340° C. to 430° C., limits included;

a partial pressure of hydrogen in the range 0.3 to 1.5 MPa, limits included, preferably in the range 0.4 to 1.2 MPa, limits included, more preferably in the range 0.7 to 1.2 MPa, limits included;

a total pressure in the range 0.45 to 1.9 MPa, limits included, preferably in the range 0.6 to 1.5 MPa, limits included;

a feed space velocity, expressed in kilograms of feed introduced per kilogram of catalyst per hour, in the range 0.25 to 30 $h^{-1}$, limits included, preferably in the range 1 to 10 $h^{-1}$, limits included, more preferably in the range 2 to 6 $h^{-1}$, limits included.

The following examples illustrate the invention without in any way limiting its scope.

EXAMPLE 1

Preparation of Catalyst C1 Containing 10.0% by Weight of EU-1 Zeolite with a Si/Al Ratio of 18.3, 89.7% of Alumina and 0.29% of Platinum.

The starting material was an as synthesised EU-1 zeolite comprising the organic template, silicon and aluminium, with a global Si/Al atomic ratio of 13.6, and a sodium content of about 1.5% with respect to the weight of dry EU-1 zeolite, corresponding to an atomic ratio Na/Al of 0.6.

This EU-1 zeolite first underwent dry calcining at 550° C. in a stream of air for 6 hours. The solid obtained underwent three ion exchange steps in a 10 N $NH_4NO_3$ solution at about 100° C. for 4 hours per exchange step.

After these treatments, the EU-1 zeolite in its $NH_4$ form had a global Si/Al atomic ratio of 18.3, a sodium content with respect to the weight of dry EU-1 zeolite of 50 ppm by weight, corresponding to a Na/Al atomic ratio of 0.003, a specific surface area measured by the BET method of 407 $m^2/g$ and a pore volume, in nitrogen, measured at –196° C. and at a $P/P_0=0.15$, of 0.16 $cm^3$ of liquid nitrogen per gram.

The EU-1 zeolite was then formed by extrusion with an alumina gel to obtain, after drying and calcining in dry air, support constituted by extrudates with 1.4 mm diameter which contained 10% by weight of EU-1 zeolite in its H form and 90% of alumina. The pore diameter of the prepared catalyst, measured using a mercury porosimeter, was in the range 40 Å to 90 Å, the distribution of the diameters of these mesopores was centred on 70 Å. The bed crush strength obtained using the Shell method was 1.1 MPa.

Support obtained underwent anion exchange with hexachloroplatinic acid in the presence of a competing agent (hydrochloric acid), to introduce 0.3% by weight of platinum with respect to the catalyst. The moist solid was then dried at 120° C. for 12 hours and calcined in a dry air stream at 500° C. for 1 hour.

Catalyst C1 obtained contained 10.0% by weight of EU-1 zeolite in its H form, 89.7% of alumina and 0.29% of platinum. The dispersion of the metallic phase was 95%, determined by chemisorption, and the platinum distribution coefficient was 0.90, determined using a Castaing microprobe.

EXAMPLE 2

Preparation of Catalyst C2 Containing 10.0% by Weight of EU-1 Zeolite with a Si/Al Ratio of 31, 89.7% of Alumina and 0.28% of Platinum.

The starting material was an as synthesised zeolite with structure type EUO, EU-1 zeolite, comprising the organic template, silicon and aluminium, with a global Si/Al atomic ratio of 28, and a sodium content of about 0.4% with respect to the weight of dry EU-1 zeolite, corresponding to an atomic ratio Na/Al of 0.30.

This EU-1 zeolite first underwent dry calcining at 550° C. in a stream of air for 6 hours. The solid obtained underwent three ion exchange steps in a 10 N $NH_4NO_3$ solution at about 100° C. for 4 hours per exchange step.

After these treatments, the EU-1 zeolite in its $NH_4$ form had a global Si/Al atomic ratio of 31, a sodium content with respect to the weight of dry EU-1 zeolite of 100 ppm by weight, corresponding to a Na/Al atomic ratio of 0.008, a specific surface area measured by the BET method of 435 $m^2/g$ and a pore volume, in nitrogen, measured at –196° C. and at a $P/P_0=0.15$, of 0.18 $cm^3$ of liquid nitrogen per gram.

The EU-1 zeolite was then formed by extrusion with an alumina gel to obtain, after drying and calcining in dry air, support constituted by extrudates with 1.4 mm diameter which contained 10% by weight of EU-1 zeolite in its H form and 90% of alumina. The pore diameter of the prepared catalyst, measured using a mercury porosimeter, was in the range 100 Å to 1000 Å, the distribution of the diameters of these mesopores being unimodal and centred on 330 Å. This difference in porosity between catalysts C1 and C2 resulted from the use of different alumina gels. The bed crush strength obtained using the Shell method was 1.0 MPa.

Support obtained underwent anion exchange with hexachloroplatinic acid in the presence of a competing agent (hydrochloric acid), to introduce 0.3% by weight of platinum with respect to the catalyst. The moist solid was then dried at 120° C. for 12 hours and calcined in a dry air stream at 500° C. for 1 hour.

Catalyst C2 obtained contained 10.0% by weight of EU-1 zeolite in its H form, 89.7% of alumina and 0.28% of platinum. The dispersion of the metallic phase was 94%, determined by chemisorption, and the platinum distribution coefficient was 0.92, determined using a Castaing microprobe.

EXAMPLE 3

Preparation of Catalyst C3 Containing 29.9% by Weight of EU-1 Zeolite with a Si/Al Ratio of close to 44, 69.8% of Alumina and 0.29% of Platinum.

The starting material was an as synthesised EU-1 zeolite comprising the organic template, silicon and aluminium, with a global Si/Al atomic ratio of about 44, and a sodium content of about 0.5% with respect to the weight of dry EU-1 zeolite, corresponding to an atomic ratio Na/Al of approximately 0.6.

This EU-1 zeolite first underwent dry calcining at 550° C. in a stream of air for 6 hours. The solid obtained underwent three ion exchange steps in a 10 N $NH_4NO_3$ solution at about 100° C. for 4 hours per exchange step.

After these treatments, the EU-1 zeolite in its $NH_4$ form had a global Si/Al atomic ratio of approximately 44, a sodium content with respect to the weight of dry EU-1 zeolite of 100 ppm by weight, corresponding to a Na/Al atomic ratio of about 0.012%, a specific surface area measured by the BET method of 420 $m^2/g$ and a pore volume, in nitrogen, measured at –196° C. and at a $P/P_0=0.15$, of 0.17 $cm^3$ of liquid nitrogen per gram.

The EU-1 zeolite was then formed by extrusion with an alumina gel to obtain, after drying and calcining in dry air, support constituted by extrudates with 1.4 mm diameter which contained 30% by weight of EU-1 zeolite in its H form and 70% of alumina. The pore diameter of the prepared catalyst, measured using a mercury porosimeter, was in the range 40 Å to 90 Å, the distribution of the diameters of these mesopores being unimodal and centred on 70 Å. The bed crush strength obtained using the Shell method was 0.89 MPa.

Support obtained underwent anion exchange with hexachloroplatinic acid in the presence of a competing agent (hydrochloric acid), to introduce 0.3% by weight of platinum with respect to the catalyst. The moist solid was then dried at 120° C. for 12 hours and calcined in a dry air stream at 500° C. for 1 hour.

Catalyst C3 obtained contained 29.9% by weight of EU-1 zeolite in its H form, 69.8% of alumina and 0.29% of platinum. The dispersion of the metallic phase was 92%, determined by chemisorption, and the platinum distribution coefficient was 0.94, determined using a Castaing microprobe.

EXAMPLE 4

Preparation of Catalyst C4 Containing 10.0% by Weight of EU-1 Zeolite with a Si/Al Ratio of 18.3, 89.6% of Alumina, 0.28% of Platinum and 0.14% of Tin.

To prepare catalyst C4, tin then platinum were deposited on support obtained in Example 1.

Tin was first deposited on the solid by ion exchange with a tin chloride $SnCl_2$ solution in the presence of a competing agent (hydrochloric acid), to obtain 0.15% by weight of tin with respect to the catalyst. Deposition was followed by calcining. A second anion exchange step was then carried out with hexachloroplatinic acid in the presence of a competing agent (hydrochloric acid), to introduce 0.3% by weight of platinum with respect to the catalyst. The moist solid was then dried at 120° C. for 12 hours and calcined in a stream of dry air at a temperature of 500° C., for 1 hour.

Catalyst C4 obtained contained 10.0% by weight of zeolite, 89.6% of alumina, 0.28% by weight of platinum and 0.14% by weight of tin. The metallic phase had a dispersion of 91%, determined by chemisorption, and a platinum distribution coefficient of 0.89, determined using a Castaing microprobe. The crush strength of catalyst C4 was the same as that measured for catalyst C1.

EXAMPLE 5

Preparation of Catalyst C5, not in Accordance with the Invention, Containing Mordenite and 0.3% by Weight of Platinum The starting zeolite was a mordenite with a Si/Al ratio of 5.2 and a unit cell volume of 2.794 $nm^3$. The zeolite underwent three ion exchange steps in a 10 N $NH_4NO_3$ solution at about 100° C. for 4 hours. The solid obtained contained 25 ppm of sodium.

This zeolite was formed by extrusion (extrusion diameter=4 mm) with an alumina gel to obtain, after drying and calcining in dry air, a support which contained 10% by weight of mordenite zeolite in its hydrogen form, and 90% of alumina.

Support underwent anion exchange with hexachloroplatinic acid in the presence of a competing agent (hydrochloric acid), to deposit 0.3% by weight of platinum with respect to the catalyst. The moist solid was then dried at 120° C. for 12 hours and calcined in a dry air stream at a temperature of 500° C. for 1 hour.

Catalyst C5 obtained contained 10.0% by weight of mordenite in its hydrogen form, 89.7% of alumina and 0.3% of platinum. The dispersion of the platinum was 95%, determined by chemisorption, and the platinum distribution coefficient was 0.95, determined using a Castaing microprobe. The pore diameter was between 40 and 90 Å, measured using a mercury porosimeter. The distribution of the diameters of these mesopores was unimodal and centred on 70 Å. The bed crush strength, obtained using the Shell method, was 1.5 MPa.

EXAMPLE 6

Preparation of Catalyst C6, not in Accordance with the Invention, Containing EU-1 Zeolite and 0.3% by Weight of Platinum Catalyst C6 was prepared using the same procedure as catalyst C1 but the final calcining step at 500° C. was left out and the preparation was finished by simple drying at 120° C.

Metallic dispersion measurement using oxygen chemisorption gave a value of 95% for catalyst C1 while a value of only 43% was obtained for catalyst C6, not in accordance with the invention.

EXAMPLE 7

Preparation of Catalyst C7, not in Accordance with the Invention, Containing EU-1 Zeolite and 0.3% of Platinum.

Catalyst C7 was obtained by peletizing a mixture of EU-1 zeolite as described in Example 1 with an alumina on which 0.33% by weight of platinum had been deposited.

Platinum was deposited on the alumina by anion exchange with hexachloroplatinic acid in the presence of a competing agent (hydrochloride acid). The moist alumina was dried at 120° C. for 12 hours and calcined in a stream of dry air at a temperature of 500° C. for one hour. The metallic phase was 99% dispersed, measured by oxygen chemisorption. Forming was then carried out by pelletizing.

Pelletized catalyst C7 obtained contained 10.0% by weight of EU-1 zeolite in its hydrogen form, 89.7% of alumina and 0.3% of platinum.

The principal difference between catalysts C1 and C7 thus resides in forming which is not in accordance in the case of catalyst C7. In the latter case, a Shell crush strength of 0.3 MPa was obtained which was substantially lower than that of sample C1.

EXAMPLE 8

Evaluation of Catalytic Properties of Catalysts C1 to C7 for Isomerisation of a $C_8$ Aromatic cut using 5 g of Catalyst The performances of catalysts C1 to C7 were evaluated for isomerisation of a $C_8$ aromatic cut containing principally meta-xylene, ortho-xylene and ethylbenzene using 5 g of catalyst. The operating conditions were as follows:

temperature: 390° C.;
total pressure: 15 bar (1 bar=0.1 MPa);
partial pressure of hydrogen: 12 bar.

The catalysts were first treated with a feed containing dimethyl disulphide (DMDS) in the presence of hydrogen, in a concentration such that the sulphur/metal atomic ratio was 1.5 except for catalyst C4. The catalyst was kept for 3 hours at 400° C. in a stream of hydrogen, then the feed was injected.

The catalysts were evaluated in terms of activity (using approximate equilibria of para-xylene and ethylbenzene, and by ethylbenzene conversion) and in terms of selectivity by net loss at iso-approximate equilibrium of para-xylene.

Side reactions result in three types of loss: loss of paraffins resulting essentially from naphthene ring opening followed by cracking, loss of aromatics formed by dismutation and transalkylation of aromatics containing 8 carbon atoms AC8, and finally loss of naphthenes, namely naphthenes containing 8 carbon atoms (N8) due to aromatic hydrogenation. Since the N8 compounds can be recycled, the loss due to cracking and dismutation/transalkylation including napthenes other than the N8 compounds (the sum constituting the net loss) is compared by taking catalyst A, not in accordance with the invention, as the base 100% for each type of loss.

To calculate approximate equilibria (AEQ), ethylbenzene concentrations (%EB) are expressed with respect to four AC8 isomers, and those of para-xylene (%pX) are expressed with respect to three xylene isomers.

The approximate equilibria (AEQ) are defined as follows:

pX AEQ (%)=100×(%pX$_{effluent}$−%pX$_{feed}$)/(%pX$_{equilibrium}$−%pX$_{feed}$)

EB AEQ (%)=100×(%EB$_{effluent}$−%EB$_{feed}$)/(%EB$_{equilibrium}$−%EB$_{feed}$)

The cracking loss (P1) is the loss of AC8 in the form of $C_1$ to $C_8$ paraffins (PAR):

P1(wt %)=100×[(%PAR$_{effluent}$×wt of effluent)−(%PAR$_{feed}$×wt of feed)]/(%AC8$_{feed}$×wt of feed)

The dismutation/transatkylation loss (P2) is the loss of AC8 in the form of naphthenes other than N8, toluene, benzene and $C_9$+aromatics (OAN):

P2(wt %)=100×[(%OAN$_{effluent}$×wt of effluent)−(%OAN$_{feed}$×wt of feed)]/(%AC8$_{feed}$×wt of feed)

The sum of losses P1 and P2 represents the net loss.

The results shown in Table 1 were obtained under experimental iso-conditions.

TABLE 1

| Catalysts | C1 | C2 | C3 | C5 not in accordance | C6 not in accordance | C7 not in accordance |
|---|---|---|---|---|---|---|
| Si/Al | 18.3 | 31 | 44 | MOR | 18.3 | 18.3 |
| Content of zeolite (%) | 10 | 10 | 30 | 10 | 10 | 10 |
| pX AEQ (%) | 98.0 | 97.1 | 97.8 | 94.5 | 97.7 | 97.9 |
| EB AEQ (%) | 90.8 | 81.2 | 87.7 | 86.2 | 66.1 | 88.8 |
| EB conversion (%) | 55.9 | 52.2 | 55.4 | 54.1 | 44.1 | 59.8 |
| Net loss (wt %) | 5.7 | 5.2 | 7.1 | 6.7 | 6.3 | 14.9 |

The results of Table 1 show that catalysts C1 to C3 in accordance with the invention were much more active than catalyst C5 which was not in accordance, since under operating iso-conditions they produced a pX AEQ of 98.0%, 97.1% and 97.8% respectively (compared with 94.5% for catalyst C5).

Moreover, catalysts C1 to C3, in accordance with the invention had a EB conversion of 55.9%, 52.2% and 55.4% respectively, which are EB conversion of much higher than catalyst C6 not in accordance with the invention (44.1%).

And catalysts C1 to C3 were more selective than catalyst C7 not in accordance with the invention, as the net less were 5.7%, 5.2% and 7.1% respectively compared to 14.9% for catalyst C7.

Further, the catalysts were compared at iso pX AEQ (about 95.5%) by varying the feed mass flow rates. These results are shown in Table 2.

TABLE 2

| Catalysts | C1 | C2 | C3 | C4 | C5 not in accordance |
|---|---|---|---|---|---|
| Si/Al | 18.3 | 31 | 44 | 18.3 | MOR |
| Content of zeolite (%) | 10 | 10 | 30 | 10 | 10 |
| pX AEQ (%) | 95.5 | 94.5 | 95.3 | 94.8 | 94.5 |
| Net loss (wt %) | 4.7 | 4.5 | 5.9 | 4.4 | 6.7 |
| cracking | 98 | 107 | 103 | 86 | 100 |
| dismutation/transalkylation | 53.6 | 43.3 | 80.4 | 56.9 | 100 |

At iso pX AEQ, Table 2 shows that catalyst C1 to C4 in accordance with the invention were also more selective than catalyst C5, not in accordance. For a pX AEQ of about 95.5%, the net loss was 4.7%, 4.5%, 5.9% and 4.4% respectively by weight for catalyst C1 to C4 compared with 6.7% by weight for catalyst C5. This very large gain in the case of catalysts of the invention can be seen to be due to the dismutation/transalkylation loss.

The activity and selectivity during use of catalysts in accordance with the invention based on a zeolite with structure EUO for isomerisation of an aromatic $C_8$ cut are thus substantially improved over the prior art.

Stability tests were also carried out. Catalysts C1 and C6 were tested under the conditions described above over 800 hours. They were then discharged and regenerated under the same conditions: they were then referred to as C1R and C6R respectively. Regeneration consisted of air treatment at a temperature of 500° C. to burn off the coke deposited on the catalyst over the 800 hours of reaction. Following regeneration, a second test of 800 hours under feed was carried out on catalysts C1R and C6R, under identical operating conditions to those of the first 800 hour test. The results are shown in Table 3.

TABLE 3

| Catalyst | C1 (in accordance) | C6 (not in accordance) |
|---|---|---|
| EB conversion (%) at t = 36h | 55.9 | 44.1 |
| EB conversion (%) at t = 800h | 53.2 | 39.4 |
| EB conversion drop (%) | 4.9 | 10.6 |

| Catalyst | C1R (in accordance) | C6R (not in accordance) |
|---|---|---|
| EB conversion (%) at t = 36h | 55.0 | 41.9 |
| EB conversion (%) at t = 800h | 51.7 | 36.8 |
| EB conversion drop (%) | 6.0 | 12.2 |

Catalyst C1, in accordance with the invention, exhibited a deactivation (measured by the drop in ethylbenzene conversion) of 4.9% for an 800 hour test. Regeneration of catalyst C1 recovered an ethylbenzene conversion of 55.0% compared with 55.9% for fresh catalyst. Catalyst C6, not in accordance with the invention, was far less stable with 10.6% deactivation for the same number of hours. Regeneration was also less effective.

This example shows that catalyst C1 of the invention in which the dispersion of the group VIII metal on the catalyst surface was good, was more active and more stable than catalyst C6, not in accordance with the invention.

EXAMPLE 9

Evaluation of Catalytic Properties of Catalysts C1 and C5 for Isomerisation of a $C_8$ Aromatic cut using 60 g of Catalyst The performances of catalysts C1 and C5 were evaluated for isomerisation of a $C_8$ aromatic cut containing principally meta-xylene, ortho-xylene and ethylbenzene using 60 g of catalyst. The operating conditions were as follows:

temperature: 375° C.;

total pressure: 9 bar (1 bar=0.1 MPa);

$H_2$/HC: 4

The results obtained, under iso pX AEQ conditions are shown in table 4.

TABLE 4

| Catalysts | C1 | C5 |
| --- | --- | --- |
| Si/Al | 18.3 | MOR |
| Content of zeolite (%) | 10 | 10 |
| pph($h^{-1}$) | 4 | 2.51 |
| pX AEQ(%) | 93.1 | 92.91 |
| EB conversion (%) | 41.0 | 46.1 |
| Net loss (wt %) | 1.6 | 4.8 |
| Cracking loss | 69 | 100 |
| dismutation/transalkylation | 20 | 100 |

It can be seen that catalyst C1 in accordance with the invention was more selective than catalyst C5 not in accordance. For a pX AEQ of about 93%, the net less was 1.6% by weight for catalyst C1 compared with 4.8% by weight for catalyst C5. Moreover, catalyst C1 is more active. For a iso pX AEQ, the feed space velocity was 4 $h^{-1}$ for C1 compared to 2.51 $h^{-1}$ for C5.

What is claimed is:

1. A catalyst in the form of balls or extrudates comprising at least one zeolite with structure type EUO, at least partially in its acid form, at least one matrix, and at least one metal from group VIII of the periodic table, the zeolite comprising silicon and at least one element T selected from the group consisting of aluminum, iron, gallium and boron, with a global Si/T atomic ratio over 5, the catalyst being characterized in that the dispersion of the group VIII metal is in the range 60% to 100%, limits included, and the macroscopic distribution coefficient of the group VIII metal is in the range 0.7 to 1.3, limits included, the catalyst having a mechanical strength such that the bed crush strength is more than 0.7 MPa said catalyst further comprising sulfur in an amount such that the ratio of the number of sulphur atoms to the number of atoms of deposited group VIII metal is in the range 0.5 to 2.

2. A process for preparing a catalyst according to claim 1, comprising a step for treating an as synthesized zeolite with structure type EUO, a step in which the matrix and said zeolite are mixed, a calcining step is carried out at a temperature in the range 250° C. to 600° C., limits included, a deposition step of said at least one group VIII metal is conducted at any time during the preparation and wherein sulphur is introduced into the formed, calcined and reduced catalyst containing the deposited element or elements, either in situ before the catalytic reaction, or ex situ.

3. A catalyst in the form of balls or extrudates comprising at least one zeolite with structure type EUO, at least partially in its acid form, at least one matrix, and at least one metal from group VIII of the periodic table, the zeolite comprising silicon and at least one element T selected from the group consisting of aluminum, iron, gallium and boron, with a global Si/T atomic ratio over 5, the catalyst being characterized in that the dispersion of the group VIII metal is in the range 60% to 100%, limits included, and the macroscopic distribution coefficient of the group VIII metal is in the range 0.7 to 1.3, limits included, the catalyst having a mechanical strength such that the bed crush strength is more than 0.7 MPa.

4. A catalyst according to claim 3, characterized in that the dispersion of the group VIII metal is in the range 70% to 100%.

5. A catalyst according to claim 3, characterized in that the macroscopic distribution coefficient is in the range 0.8 to 1.2.

6. A catalyst according to claim 3, characterized in that the zeolite with structure type EUO is EU-1 zeolite.

7. A catalyst according to claim 3, characterized in that the element T is aluminum or boron.

8. A catalyst according to claim 3, characterized in that the matrix is alumina.

9. A catalyst according to claim 3, characterized in that the group VIII metal is platinum or palladium.

10. A catalyst according to claim 3, characterized in that the zeolite is at least partially in its acid form with a Na/T atomic ratio of below 0.5.

11. A catalyst according to claim 3, characterized in that it contains 1% to 90% by weight of at least one zeolite with structure type EUO.

12. A catalyst according to claim 11, wherein said catalyst comprises 3% to 60% by weight of said at least one zeolite with structure type EUO.

13. A catalyst according to claim 11, wherein said catalyst comprises 4% to 40% by weight of said at least one zeolite with structure type EUO.

14. A catalyst according to claim 3, characterized in that the concentration of group VIII metal or metals is in the range 0.01% to 2.0% by weight, with respect to the total catalyst weight.

15. A catalyst according to claim 3, characterized in that it further comprises at least one element selected from the group consisting of groups IIIA and IVA of the periodic table.

16. A catalyst according to claim 3, characterized in that the element selected from the group consisting of groups IIIA and IVA of the periodic table is tin and/or indium.

17. A catalyst according to claim 3, characterized in that the concentration of said at least one element selected from the group formed by groups IIIA and IVA of the periodic table is in the range 0.01% to 2.0%, with respect to the catalyst.

18. A catalyst according to claim 3, characterized in that it comprises sulphur in an amount such that the ratio of the number of sulphur atoms to the number of atoms of deposited group VIII metal is in the range 0.5 to 2.

19. A process for preparing a catalyst according to claim 3, comprising a step for treating an as synthesised zeolite with structure type EUO, a step in which the matrix and said zeolite are mixed then said mixture is formed, and a calcining step is carried out at a temperature which is in the range 250° C. to 600° C., limits included, and a deposition step of said at least one group VIII metal can be carried out at any time during the preparation.

20. A process for preparing a catalyst according to claim 19, in which deposition of the group VIII metal is followed by calcining carried out at a temperature which is in the range 250° C. to 600° C.

21. A process according to claim 19, characterized in that the group VIII metal is deposited after the calcining step which follows forming of the matrix-zeolite mixture.

22. A process according to claim 19, characterized in that more than 90% of the group VIII metal is completely deposited on the matrix.

23. A process according to claim 19, characterized in that it comprises depositing at least one element selected from the group consisting of elements from groups IIIA and IVA, deposition being carried out at any time during the preparation.

24. A process according to claim 19, characterized in that said at least one element selected from the group consisting of elements from groups IIIA and IVA is deposited before depositing the group VIII metal.

25. A process according to claim 19, characterized in that sulphur is introduced into the formed, calcined and reduced catalyst containing the deposited element or elements, either in situ before the catalytic reaction, or ex situ.

26. A process according to claim 19, wherein said depositing is conducted by anionic ion exchange.

27. A process according to claim 26, wherein said depositing is conducted by anionic ion exchange.

28. A catalyst produced in accordance with claim 27, and wherein more than 90% of the group VIII metal is completely deposited on the matrix and said group VIII metal is platinum.

29. A process according to claim 26, wherein the group VIII metal is platinum.

30. A process according to claim 19, wherein the group VIII metal is platinum.

31. In a process for catalytically isomerizing aromatic compounds containing 8 carbon atoms per molecule, the improvement wherein the catalyst is according to claim 3.

32. A process according to claim 31, characterized in that the feed is selected from a mixture of xylenes, from ethylbenzene, and from a mixture of xylenes and ethylbenzene.

33. A process according to claim 31, characterized in that it is carried out at a temperature in the range 300° C. to 500° C., at a partial pressure of hydrogen which is in the range 0.3 to 1.5 MPa, at a total pressure which is in the range 0.45 to 1.9 MPa and at a supply space velocity in the range 0.25 to 30 $h^{-1}$.

34. A catalyst according to claim 3, wherein more than 90% of the group VIII metal is completely deposited on the matrix.

35. A process for preparing a catalyst according to claim 3, comprising the following sequential steps:
   a) mixing said zeolite with a structure type EUO with a matrix,
   b) forming said mixture into extrudates or balls,
   c) calcining the resultant mixture at a temperature in the range of 250° to 600° C., limits included,
   d) depositing at least one group VIII metal on the calcined mixture, and
   e) further calcining the resultant catalyst at a temperature in the range of 250° to 600° C., limits included.

36. A process according to claim 35, wherein the group VIII metal is platinum.

37. A catalyst according to claim 3, wherein the group VIII metal is platinum.

* * * * *